United States Patent
Serafin, Jr. et al.

(10) Patent No.: US 9,078,754 B1
(45) Date of Patent: Jul. 14, 2015

(54) HARDER-SOFTER HARD SUBSTANCE ARTICULATION FOR ARTHROPLASTY

(75) Inventors: Louis A. Serafin, Jr., Lakeport, MI (US); Nicholas H. Burlingame, Belmont, NY (US); Gerald J. Jerry, Jr., St. Clair, MI (US)

(73) Assignee: Signal Medical Corporation, Marysville, MI (US)

( * ) Notice: Subject to any disclaimer, the term of this patent is extended or adjusted under 35 U.S.C. 154(b) by 749 days.

(21) Appl. No.: 11/401,394

(22) Filed: Apr. 10, 2006

Related U.S. Application Data

(60) Provisional application No. 60/676,668, filed on Apr. 29, 2005, provisional application No. 60/714,706, filed on Sep. 7, 2005.

(51) Int. Cl.
*A61F 2/28* (2006.01)
*A61F 2/32* (2006.01)
*A61F 2/38* (2006.01)
*A61F 2/30* (2006.01)

(52) U.S. Cl.
CPC ... *A61F 2/32* (2013.01); *A61F 2/38* (2013.01); *A61F 2002/30016* (2013.01); *A61F 2002/30649* (2013.01); *A61F 2002/3208* (2013.01); *A61F 2310/00197* (2013.01); *A61F 2310/00239* (2013.01)

(58) Field of Classification Search
CPC ............ A61F 2310/00239; A61F 2310/00197; A61F 2310/00089
USPC .......................... 623/23.56, 18.11, 23.39, 23.4
See application file for complete search history.

(56) References Cited

U.S. PATENT DOCUMENTS

| | | | | |
|---|---|---|---|---|
| 4,636,218 A | * | 1/1987 | Fukuura et al. | 623/18.11 |
| 4,826,612 A | * | 5/1989 | Habeeb et al. | 508/378 |
| 4,885,266 A | * | 12/1989 | Hughan et al. | 501/104 |
| 5,183,068 A | * | 2/1993 | Prosser | 137/1 |
| 5,258,022 A | * | 11/1993 | Davidson | 623/2.42 |
| 5,458,648 A | * | 10/1995 | Berman et al. | 623/21.19 |
| 5,648,127 A | | 7/1997 | Turchan et al. | |
| 5,865,850 A | * | 2/1999 | Matthews | 623/22.43 |
| 5,871,547 A | | 2/1999 | Abouaf et al. | 623/22 |
| 5,879,407 A | * | 3/1999 | Waggener | 623/23.4 |
| 6,096,084 A | * | 8/2000 | Townley | 623/23.12 |

(Continued)

FOREIGN PATENT DOCUMENTS

WO   WO 2004/080340 A2 * 9/2004

OTHER PUBLICATIONS

CeramConcept, 3DΔ (TM) device advertisement, *Orthopedics Today*, p. 45, ca. 2006.

(Continued)

*Primary Examiner* — Thomas J Sweet
*Assistant Examiner* — Cheryl Miller
(74) *Attorney, Agent, or Firm* — Christopher John Rudy

(57) ABSTRACT

Hard substance wear couple has materials of differing hardness forming surfaces for articulation in a joint implant prosthesis. For instance, a first articulating body can have a convex articulating surface, and a second articulating body can have a corresponding concave articulating surface that can articulate with the convex articulating surface of the first articulating body, in which the convex articulating surface of the first articulating body is harder than the corresponding concave articulating surface of the second articulating body. Ceramic materials are preferred.

20 Claims, 1 Drawing Sheet

(56) References Cited

U.S. PATENT DOCUMENTS

| | | | | |
|---|---|---|---|---|
| 6,165,925 | A | * | 12/2000 | Rieger .................... 501/103 |
| 6,387,132 | B1 | * | 5/2002 | Deppisch et al. .......... 623/22.11 |
| RE37,964 | E | * | 1/2003 | Prats et al. ............... 623/23.11 |
| 6,626,949 | B1 | | 9/2003 | Townley |
| 7,037,603 | B2 | * | 5/2006 | Lasater .................... 428/701 |
| 7,666,229 | B2 | * | 2/2010 | Khandkar ................ 623/22.15 |
| 7,790,216 | B2 | * | 9/2010 | Popoola et al. ........... 427/2.27 |
| 7,820,577 | B2 | * | 10/2010 | Shikata et al. ............ 501/105 |
| 7,981,160 | B1 | * | 7/2011 | Serafin et al. ............ 623/22.25 |
| 2002/0010070 | A1 | * | 1/2002 | Cales et al. ............... 501/105 |
| 2002/0165615 | A1 | * | 11/2002 | Abouaf et al. ............ 623/22.21 |
| 2002/0198602 | A1 | * | 12/2002 | Nawa et al. .............. 623/23.56 |
| 2005/0033442 | A1 | * | 2/2005 | Fisher et al. ............. 623/18.11 |
| 2005/0107888 | A1 | * | 5/2005 | Khandkar et al. ........ 623/23.39 |
| 2005/0187638 | A1 | * | 8/2005 | Glien et al. .............. 623/23.56 |
| 2006/0085079 | A1 | * | 4/2006 | Carroll ..................... 623/22.15 |
| 2006/0259144 | A1 | * | 11/2006 | Trieu ....................... 623/17.13 |
| 2008/0215158 | A1 | * | 9/2008 | Pope et al. ............... 623/22.16 |
| 2008/0275568 | A1 | * | 11/2008 | Shikata et al. ............ 623/23.56 |
| 2009/0012611 | A1 | * | 1/2009 | Brosnahan et al. ....... 623/11.11 |

OTHER PUBLICATIONS

CeramConcept website (www.ceramconcept.com), 2005, Home, Epidemiology, and the three Ceramic Self Adjusting Cup pages, downloaded May 23, 2006.

Serafin, Jr., et al., U.S. Appl. No. 60/676,668, filed Apr. 29, 2005 A.D.

Jerry, Jr., et al., U.S. Appl. No. 60/714,706, filed Sep. 7, 2005 A.D.

ASTM International, ASTM F 2393-04, 2 pp., Jun. 2004.

Clarke et al., *Proc. Instn.Mech.Engrs.*, vol. 214, Part H, pp. 331-347, 2000.

Früh et al. PubMed Abstract, *Biomaterials*, vol. 17 No. 22, 2157-2162, Nov. 1996 (1 p.).

Früh et al. PubMed Abstract, *Biomaterials*, vol. 18 No. 12, 873-876, Jun. 1997 (1 p.).

Roy et al., *J. Biomedical Matls. Res.*, Part A, Wiley InterScience, 1096-1102, Jun. 21, 2007.

Roy et al., *Clin. Orthopaedics Rel. Res.*, No. 465, 220-226, Dec. 2007.

Roy et al., *Clin. Orthopaedics Rel. Res.*, published online Feb. 11, 2011, 9 pp.

Stewart et al., PubMed Abstract, *J. Arthroplasty*, vol. 18, No. 6, 726-734, Sep. 2003 (1 p.).

Tipper et al., PubMed Abstract, *Biomaterials*, vol. 23, No. 16, 3441-3448, Aug. 2002 (1 p.).

McKechnie et al. (Eds.), Webster's New Universal Unabridged Dictionary, Deluxe Second Edition, Dorset & Baber, Cleveland, Ohio, 1983, p. 592.

Superior Technical Ceramics, "Magnesia Stabilized Zirconia (MSZ): Why Does MSZ Have a Better High Temperature Strength than YTZP?" www.ceramics.net, 2014, 2 pages, printed.

Wikipedia, "Scratch hardness," last modified Oct. 4, 2014, 2 pages, printed Dec. 29, 2014.

\* cited by examiner

US 9,078,754 B1

HARDER-SOFTER HARD SUBSTANCE ARTICULATION FOR ARTHROPLASTY

This claims benefits under 35 USC 119(e) of provisional application Nos. 60/676,668 filed on Apr. 29, 2005 A.D., and 60/714,706 filed on Sep. 7, 2005 A.D. The complete specifications of those applications are incorporated herein by reference.

FIELD AND PURVIEW OF THE INVENTION

The present invention concerns a hard substance wear couple having materials of differing hardness forming surfaces for articulation in a joint implant prosthesis. Such a wear couple can include a ceramic-on-ceramic, composite-on-composite, metal-on-metal, or mixed hard substance wear couple. Ceramic materials are preferred.

BACKGROUND TO THE INVENTION

Wear and wear debris are leading causes of implant failure. This has resulted in a very serious interest among surgeons to obtain implants which produce less debris. In particular, ultra high weight polyethylene (UHMWPE) is used extensively in total joint replacement surgery as an articulating surface. This material, however, is prone to wear, producing debris which has been negatively associated with the long term fixation of replacement devices. For instance, Cobalt-Chromium alloy (Co—Cr) heads or condyles, or certain zirconia or alumina heads, articulating against an UHMWPE cup or liner form part of standard ensembles for various total replacement joints, but in recent years it has been reported that polyethylene debris may induce a destructive biologic reaction, osteolysis, which may cause aseptic loosening of the implant and lead to its failure.

More particularly, for example, typical articulating materials for total joint replacements for hip joints include an UHMWPE acetabular cup and a Co—Cr alloy femoral head. Serious clinical problems with this system have been reported to be related to wear of the UHMWPE cup. The harmful effects of polyethylene wear debris have been studied extensively. Biologic reaction to the debris can cause the osteolysis leading to aseptic loosening of the implant. The result is the patient's host bone deteriorates requiring revisional surgery to replace the implant.

The rate of wear of the cup is dependent on the wear mechanism. Least aggressive wear occurs when the prosthesis functions in a stable mode, without third body interactions. In this case, the debris produced is primarily submicron sized. Typical rates of well functioning cups are 0.05~0.20 mm/year, with estimates of ~500,000 particles produced per step taken. Rapid wear can occur when third body particles such as dislodged bone cement, dislodged porous coating, or bone chips initiate abrasive wear. These can abrade the UHMWPE directly and roughen the Co—Cr head, both of which increase the wear rate of the polyethylene.

To reduce the problem of such polyethylene wear, ceramic femoral heads have been utilized as a wear couple against the UHMWPE. One major advantage of ceramics over metals is a superior surface. Ceramic materials can be polished to and maintain a smoother surface finish than metal. They also are harder, and thus less likely to incur surface damage, more chemically stable, often more biocompatible, and have a lower friction coefficient when mated with UHMWPE. Studies indicate reductions in wear rate of 30~400% over the metal-UHMWPE couples. In general, wear studies have indicated that zirconia materials are similar or better than alumina when mated to polyethylene cups.

While use of ceramic femoral heads instead of metal heads is a substantial improvement, a significant amount of polyethylene debris is still generated.

Thus, an articulating wear couple which eliminates the UHMWPE would be desirable.

And so, metal-on-metal and ceramic-on-ceramic wear couples have been proposed.

Ceramic is a notably desirable implant material.

In particular, for total hip replacements, the use of an alumina ball and an alumina cup is known, and it can result in greatly reduced wear rates. Rates of 0.002 to 0.005 mm/year have generally been reported for such well functioning implants, with some reported to be as low as 0.000025 mm/year. However, in some cases, fairly rapid and non uniform wear can occur. These poor results have been attributed to design and installation problems such as implant migration, poor initial alignment, and implant loosening; and to material problems. The enhanced wear can be related to excessive Hertzian contact stresses, which initiate wear, which is followed by a cascade-like wear process as the surfaces roughen and debris is generated. Design and installation problems suggest that the current alumina-alumina combinations are less tolerant of orientation difficulties than implants employing polyethylene cups. Additionally, there are some strength concerns with alumina. Many surgeons are hesitant to use it due to a history of head and cup failures.

In another field, the field of industrial ball valve components, a well established practice is to employ a softer ceramic against a harder ceramic. The harder head wears slightly less than the softer seat. The end result is, with proper selection of materials, the same total wear as a well matched hard couple of the same hardness. It allows the system to "wear in," reducing stresses in any high contact stress areas after installation.

It is known to employ a TZP zirconia ceramic hip ball in an alumina cup. That softer ball in harder cup couple, however, has its drawbacks. Among these, since that ball is dressed by the cup and gets smaller, it may yield a smaller ball in the cup over time, which may "rattle around."

Nevertheless, it remains desirable to improve the instant art, noting especially the ever present desire of surgeons and their patients for better and better joint implant performance.

A FULL DISCLOSURE OF THE INVENTION

In general, the present invention provides a hard substance wear couple having materials of differing hardness forming surfaces for articulation in a joint implant prosthesis. Examples of such a wear couple can include a ceramic-on-ceramic, composite-on-composite, metal-on-metal, or mixed hard substance wear couple. A ceramic-on-ceramic wear couple is preferred. Notably if the wear couple is a ball and socket joint, especially of dissimilar ceramics, desirably, the ball is harder than the socket. The invention accordingly provides an improved wear system for multi-component, including total, joint implants.

The invention is useful in arthroplasty.

Significantly, by the invention, the art is improved in kind. More particularly, a long term stable wear couple with significantly reduced production of wear debris is made available to the art for the use of surgeons and their patients. The system can incorporate the latest in materials which can provide for such fulfillments in the lacks and needs of the art.

Numerous further advantages attend the invention.

The drawings form part of the specification hereof. With respect to the drawings, which are not necessarily drawn to scale, the following is briefly noted:

Figure 1:
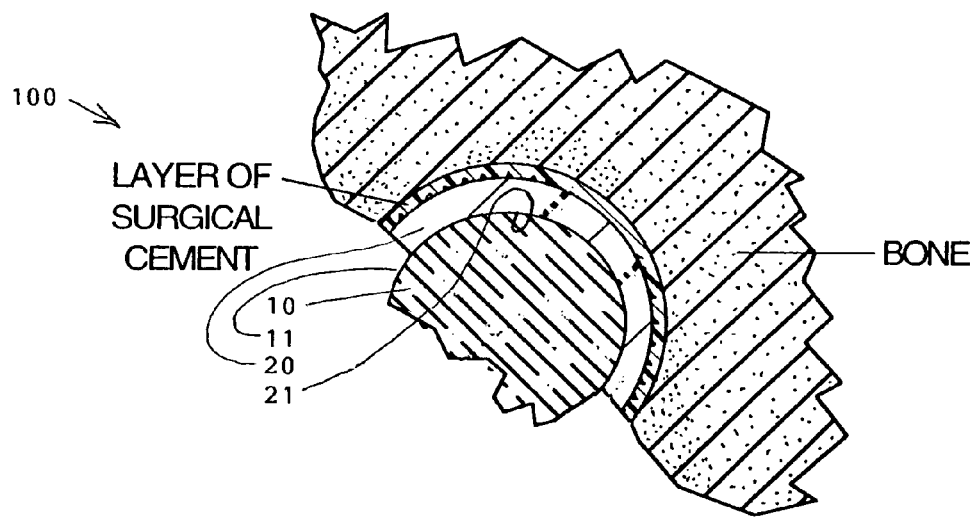
FIG. 1 shows a total enarthrodial type replacement joint implant of the invention, embodied as a total hip replacement implant.
Figure 2:
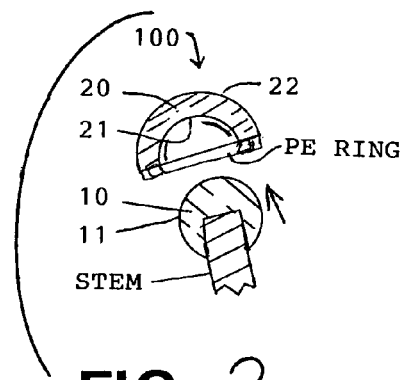
FIG. 2 shows a bipolar ceramic hip implant of the invention.
Figure 3:
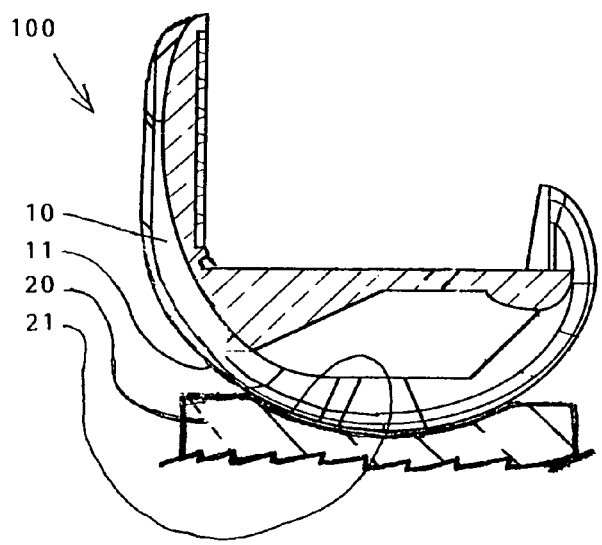
FIG. 3 shows a total ginglymous type replacement joint implant of the invention, embodied as a total knee replacement implant.

The invention can be further understood by the additional detail set forth below. The same is to be taken in an illustrative and not necessarily limiting sense.

In the genesis of the invention, to propose an improved wear system it is first necessary to define probable damage mechanisms for "hard face materials." There are several types of contact damage which are possible. These include the following:

1. Plastic removal: In this case a surface is plastically deformed, forming grooves. Some of the plastically displaced material can be in the form of particulate wear debris. This debris is formed by fracture, but plastic deformation controls the rate of removal. The source of the plastic removal process is typically associated with surface aspirates and third body particulate debris. For hard materials, the debris is typically small and the process slow in comparison to direct fracture mechanisms. Important considerations include geometric factors, material properties of both of the materials, speed, and lubrication.

To minimize wear, a system should have smooth, well matched surfaces with well distributed loads.

Also, the design should allow the surfaces to remain well matched as they wear and to take advantage of any available lubricant.

2. Indent Fracture: Elastic-plastic contact can occur between a sharp indenter and another solid. The depth of the elastic-plastic indentation will increase with applied load. At a critical size cracks can be generated. Even at sub-critical levels some micro-cracking may occur. The cracks propagate from the plastic zone under the indentation. Certain types of cracks (lateral) generated in this fashion can propagate to the surface or combine with other similarly generated cracks to form wear debris. This type of wear can be very rapid, and the debris generated can induce further wear. For this type of fracture, cracks lengths scale with indent size, with the indent size increasing with load and decreasing with hardness. Their generation and size are also a function of the fracture toughness of a material, with higher toughness inhibiting crack initiation and growth.

To minimize wear, components should have a high toughness.

And again, to minimize wear, loads should be minimized; a system should have smooth well matched surfaces; and the design should allow the surfaces to remain well matched as they wear.

3. Hertzian contact stress induced fracture: These stresses arise from the strictly elastic contact between a "blunt" indenter and another surface. Tensile stresses are highest just outside the contact area between the two surfaces. When stresses are high enough, local fracture can occur. With cyclic loading, cracks can grow and intersect, creating wear debris. For a ball and cup arrangement, for example, the stresses are reduced with close tolerances, and with lower elastic modulus materials.

To minimize wear, components should have an elastic modulus that is as low as practically possible.

Also, the system should be designed to spread the load as much as possible.

And again, to minimize wear, a system should have smooth well matched surfaces; and the design should allow the surfaces to remain well matched as they wear.

4. Thermal shock: Frictional heating and subsequent cooling can induce high stresses, which generate cracks and eventually wear debris. It is often a much localized effect at a surface asperity that develops high flash temperatures.

Again, to minimize wear, a system should have smooth well matched surfaces; and the design should allow the surfaces to remain well matched as they wear.

5. Environment: The presence of reactive fluids such as water, body saline, and so forth in a tribological system often induces stress corrosion assisted wear. In some cases, the applied stress aids in the conversion of a surface to a reaction product which can be dislodged. In others the high local stresses enhance chemically assisted crack growth. For Y-TZP materials, for example, there is also the concern of chemically induced phase transformation (tetragonal to monoclinic). In this case, water apparently enters the near surface region neutralizing the phase stabilizing effect of the $Y_2O_3$. With sufficient reaction, nuclei for transformation are produced.

To minimize wear, a system should be chemically stable in use in the body.

6. Fatigue: Under cyclic loading, a ceramic material may experience a transition to high wear at extended times. This is due to the extension of small defects until material is removed. As the material roughens the process is accelerated.

Again, to minimize wear, a system should have smooth well matched surfaces; and the design should allow the surfaces to remain well matched as they wear.

7. Boundary conditions: Wear in ceramics is characterized by transitions in wear mechanisms with variations in operating conditions. A change in wear mechanism often drastically affects wear rate. For a given wear couple, typical factors which influence the wear mechanism include contact stress, sliding speed, time, and environmental conditions.

In the selection of a wear couple, it is important that the low wear boundary conditions of its components are well within the operating conditions of the application.

To sum up, in general, to yield low wear, factors such as follows should be kept in mind:

1. Loads should be minimized much as possible by using materials and designs that:

Keep the elastic modulus as low as practically possible.

Have smooth, well matched surfaces.

Have surfaces that remain well matched as they wear.

2. The material should have: High toughness.

Resistance to environmental effects.

As the hard substance ceramics, composites, metals and alloys, and so forth may be employed. In general, for a prosthetic implant, the hard substance is biocompatible. Preferably, the hard substance is a ceramic.

As the ceramics, ceramics from "A" to "Z" may be mentioned, to include alumina and zirconia ceramics. Thus, such ceramics can include those known in the art and those described by Serafin, Jr., et al., in International patent publication No. WO 2004/080340. In ceramics, in general, certain zirconia ceramics have demonstrated improvement over alumina. High quality zirconia can often be polished to a better surface finish than alumina. It is stronger, tougher and yet easier to machine when finished than alumina. It therefore can be a more versatile material with which to design, but alumina is not necessarily debilitating. However, as disclosed by Serafin, Jr., et al. above, the ceramic can be machined green and then fired to yield a final ceramic implant product with little if any machining. Of the zirconia ceramics, a magnesium oxide (MgO) stabilized transformationally toughened zirconia (TTZ) having about from two to five percent by weight MgO is a desired component of the wear couple. When employed in the wear couple, the ceramic components can embrace different or similar ceramics. Thus, for instance, a wear couple can embrace a harder alumina component and a softer zirconia component, for example, an alumina femoral ball head and an MgO-TTZ, e.g., with about from 3.1 to 3.4 wt. % MgO, acetabular cup. On the other hand, for instance, a wear couple can embrace two zirconia ceramic materials of slightly differing hardness, one of which, say, the softer of the two, serving to form a concave articulating surface such as an enarthrodial joint cup or a ginglymous joint meniscus or the like, and the other, the harder of the two, serving to form a complimentary convex articulating surface such as an enarthrodial joint ball head or a ginglymous joint condyle or condyle pair or the like. And so, for example, with respect to the hip, the wear couple can embrace one zirconia alloy as the femoral head and another zirconia based material as the cup portion, with the zirconia materials tailored to provide a slightly harder material for the femoral head. The mismatch in hardness biases any wear to the cup portion, thus enhancing the "fit" of the system reducing the content stresses, and thereby reducing the potential for further wear.

As the composites, any suitable composite may be employed. As with the ceramics, one component of the wear couple is softer than the other, which may be provided by different or similar composites.

As the metals and alloys may be mentioned Titanium and its alloys such as 6-4-1 ELI, Cobalt and its alloys such as Co—Cr, and stainless steel. As with the ceramics and composites, one component of the wear couple is softer than the other, which may be provided by different or similar metals or alloys.

Mixed hard substance materials may be employed. For example, a ceramic may be employed to articulate against a suitable composite, metal or alloy; and so forth. As with the wear couples of similar substances, one component of the wear couple is softer than the other.

As alluded to above, zirconia ceramics are a preferred type of ceramic hard substance. The excellent mechanical properties of TTZ ceramics and the range of ceramic alloys that can be formed allow tailoring these materials for specific part requirements. A zirconia based alloy system can be employed to advantage. Zirconia alloys are much stronger than alumina. Additionally, these materials generally have lower elastic moduli, which would increase contact areas (decrease contact stress) by approximately 50% over an alumina system. Additionally, the zirconia based system is very versatile; by varying the amount and type of alloy additives and heat treatments, a range of properties can be obtained. Again, although a softer ball could be employed than the cup, use of modified zirconia alloys such that the cup is slightly softer than the ball has benefits. Fit can be maintained as the unit "wears in." The harder head will wear slightly less than the softer seat. The end result is, with proper selection of materials, the same if not superior total wear as a well matched hard couple of the same hardness. Like the well established practice in the production of industrial ball valve components, this allows the system to "wear in," reducing stresses in any high contact stress areas after "installation," i.e., implantation, but in the patient's body.

Both surfaces should be precision formed, for example, in the case of ball joints, lapped, to insure excellent surface finish and, in the case of a ball, sphericity. For a ball to rotate in a cup, the ball's outer diameter must be smaller than the inner diameter of the cup. The degree of mismatch will greatly affect the effective contact area, with close tolerances giving the best load distribution. A typical diameter mismatch is in the 25~150 μm range. Even over this small range, the effective surface contact generally varies by a factor of 2.5×. A practical limit is imposed as too close of fit will require excessive force to rotate the ball. Too loose of fit will reduce the constraint on the ball, allowing excessive translation as the ball rotates, with a reduction in contact area.

The materials selected can be from zirconia alloys similar to those which are presently used for femoral heads. For example, two types of Mg-PSZ, MgO-TTZ, or Y-TZP based materials may be employed. An MgO-TTZ may be coupled with a Y-TZP ceramic. A zirconia ceramic can be coupled with a harder alumina.

With reference to the drawings, wear couple 100 includes first articulating body 10, which may have convex articulating surface 11, and second articulating body 20, which may have corresponding concave articulating surface 21. The first and second bodies 10, 20 can be of ceramic, with the body 10 harder than the body 20. Additional articulating surface 22 may be present, for example, with bipolar hip implant so as to articulate with a natural acetabulum.

The present invention is thus provided. Various features, parts, steps subcombinations or combinations can be employed with or without reference to other features, parts, steps, subcombinations and combinations in the practice of the invention, and numerous adaptations and modifications can be effected within its spirit, the literal claim scope of which is particularly pointed out as follows:

What is claimed is:

1. A hard substance wear couple, for a joint implant prosthesis, which comprises:
    a first zirconia ceramic containing articulating body for articulation on a second zirconia ceramic containing articulating body; and
    the second zirconia ceramic containing articulating body; wherein:
        the first and second zirconia ceramic containing articulating bodies are of differing hardness and include respective first and second zirconia articulating surfaces for articulation in the wear couple in a joint implant prosthesis, which thus also are of differing hardness;
        an MgO-TTZ ceramic makes up both of the first and second articulating bodies such that MgO-TTZ articulates against MgO-TTZ; and
        the hard substance wear couple is useful in or as the joint implant prosthesis—
    and wherein the first articulating body has a convex articulating surface, and the second articulating body has a corresponding concave articulating surface that can articulate with the convex articulating surface of the first articulating body, wherein, the convex articulating surface of the first articulating body is harder than the corresponding concave articulating surface of the second articulating body, and wherein the first articulating body embraces the first zirconia containing articulating body, and the second articulating body embraces the second zirconia containing articulating body.

2. The wear couple of claim 1, wherein the joint implant prosthesis is selected from the group consisting of a total hip joint implant with an acetabular, component, which is to be affixed to a patient; a bipolar hip joint implant; and a total knee joint implant.

3. The wear couple of claim 2, which is the bipolar hip joint implant, wherein the second articulating body also has on a side opposite its concave articulating surface a convex articulating surface to articulate with a natural acetabulum.

4. The wear couple of claim 2, which is the total knee joint implant, wherein the MgO-TTZ ceramic has about from 2 to 5 percent by weight MgO.

5. The wear couple of claim 1, wherein the MgO-TTZ ceramic has about from 2 to 5 percent by weight MgO.

6. A hard substance wear couple for a joint implant prosthesis, which comprises:
a first zirconia ceramic containing articulating body for articulation on a second zirconia ceramic containing articulating body; and
the second zirconia ceramic containing articulating body;
wherein:
the first and second zirconia ceramic containing articulating bodies are of differing hardness and include respective first and second zirconia articulating surfaces for articulation in the wear couple in a joint implant prosthesis, which thus also are of differing hardness;
an MgO-TTZ ceramic makes up both of the first and second articulating bodies such that MgO-TTZ articulates against MgO-TTZ;
the hard substance wear couple is useful in or as the joint implant prosthesis;
the first articulating body has a convex articulating surface, and the second articulating body has a corresponding concave articulating surface that can articulate with the convex articulating surface of the first articulating body, wherein the convex articulating surface of the first articulating body is harder than the corresponding concave articulating surface of the second articulating body, and wherein the first articulating body embraces the first zirconia containing articulating body, and the second articulating body embraces the second zirconia containing articulating body; and
the convex articulating surface has a mismatch with the concave articulating surface, being about from 25 to 150 μm less than the concave articulating surface, such that effective surface contact between the convex articulating surface and the concave articulating surface generally varies by a factor of 2.5×.

7. The wear couple of claim 6, wherein the joint implant prosthesis is a total, hip joint implant with an acetabular component, which is to be affixed to a patient.

8. The wear couple of claim 7, wherein the MgO-TTZ ceramic has about from 2 to 5 percent by weight MgO.

9. The wear couple of claim 8, wherein the MgO-TTZ ceramic has about from 3.1 to 3.4 percent by weight MgO.

10. The wear couple of claim 6, wherein the joint implant prosthesis is a bipolar hip joint implant.

11. The wear couple of claim 10, wherein the MgO-TTZ ceramic has about from 2 to 5 percent by weight MgO.

12. The wear couple of claim 11, wherein the MgO-TTZ ceramic has about from 3.1 to 3.4 percent by weight MgO.

13. The wear couple of claim 6, wherein the joint implant prosthesis is a total knee joint implant.

14. The wear couple of claim 13, wherein the MgO-TTZ ceramic has about from 2 to 5 percent by weight MgO.

15. The wear couple of claim 14, wherein the MgO-TTZ ceramic has about from 3.1 to 3.4 percent by weight MgO.

16. The wear couple of claim 6, wherein the MgO-TTZ ceramic has about from 2 to 5 percent by weight MgO.

17. The wear couple of claim 16, wherein the MgO-TTZ ceramic has about from 3.1 to 3.4 percent by weight MgO.

18. A hard substance wear couple for a joint implant prosthesis, which comprises:
a first zirconia ceramic containing articulating body for articulation on a second zirconia ceramic containing articulating body; and
the second zirconia ceramic containing articulating body;
wherein:
the first and second zirconia ceramic containing articulating bodies are of differing hardness and include respective first and second zirconia articulating surfaces for articulation in the wear couple in a joint implant prosthesis, which thus also are of differing hardness;
an MgO-TTZ ceramic makes up both of the first and second articulating bodies such that MgO-TTZ articulates against MgO-TTZ;
the first articulating body has a convex articulating surface, and the second articulating body has a corresponding concave articulating surface that can articulate with the convex articulating surface of the first articulating body, wherein the convex articulating surface of the first articulating body is harder than the corresponding concave articulating surface of the second articulating body, and wherein the first articulating body embraces the first zirconia containing articulating body, and the second articulating body embraces the second zirconia containing articulating body;
the hard substance wear couple is useful in or as the joint implant prosthesis; and
the joint implant prosthesis is selected from the group consisting of an enarthrodial joint implant, and a ginglymous joint implant—
wherein the convex articulating surface has a mismatch with the concave articulating surface, being about from 25 to 150 μm less than the concave articulating surface, such that effective surface contact between the convex articulating surface and the concave articulating surface generally varies by a factor of 2.5×.

19. The wear couple of claim 18, wherein the MgO-TTZ ceramic has about from 2 to 5 percent by weight MgO; and the joint implant prosthesis is the enarthrodial joint implant.

20. The wear couple of claim 18, wherein the MgO-TTZ ceramic has about from 2 to 5 percent by weight MgO; and the joint implant prosthesis is the ginglymous joint implant.

\* \* \* \* \*

UNITED STATES PATENT AND TRADEMARK OFFICE
CERTIFICATE OF CORRECTION

| | |
|---|---|
| PATENT NO. | : 9,078,754 B1 |
| APPLICATION NO. | : 11/401394 |
| DATED | : July 14, 2015 |
| INVENTOR(S) | : Serafin, Jr. et al. |

It is certified that error appears in the above-identified patent and that said Letters Patent is hereby corrected as shown below:

On the title page, item [73] should read:

> Signal Medical Corporation,
> Marysville, MI (US), a part
> interest from Louis A. Serafin, Jr.
> and Nicholas H. Burlingame Signed and Sealed this
Seventh Day of June, 2016

Michelle K. Lee
*Director of the United States Patent and Trademark Office*